(12) United States Patent
Lawrence et al.

(10) Patent No.: US 12,416,592 B2
(45) Date of Patent: Sep. 16, 2025

(54) SOIL CARBON SENSOR AND SENSING ARRANGEMENT

(71) Applicant: SENSORC PTY LTD, Nedlands (AU)

(72) Inventors: Wesley Lawrence, Osborne Park (AU); Ashok Giri, Osborne Park (AU); Shalini Prasad, Richardson, TX (US); Vikram Narayanan Dhamu, Richardson, TX (US)

(73) Assignee: SENSORC PTY LTD, Nedlands (AU)

( * ) Notice: Subject to any disclaimer, the term of this patent is extended or adjusted under 35 U.S.C. 154(b) by 0 days.

(21) Appl. No.: 18/997,293

(22) PCT Filed: Jul. 25, 2023

(86) PCT No.: PCT/AU2023/050676
§ 371 (c)(1),
(2) Date: Jan. 21, 2025

(87) PCT Pub. No.: WO2024/020629
PCT Pub. Date: Feb. 1, 2024

(65) Prior Publication Data
US 2025/0258120 A1    Aug. 14, 2025

(30) Foreign Application Priority Data
Jul. 26, 2022  (AU) ............................. 2022902091

(51) Int. Cl.
*G01N 27/02* (2006.01)
*G01N 5/04* (2006.01)
(Continued)

(52) U.S. Cl.
CPC ............. *G01N 27/02* (2013.01); *G01N 5/045* (2013.01); *G01N 27/30* (2013.01); *G01N 33/246* (2013.01); *G01N 27/49* (2013.01)

(58) Field of Classification Search
CPC ........ G01N 33/24; G01N 27/02; G01N 27/30; G01N 27/49; G01N 5/045; G01N 33/246; A01B 79/02
See application file for complete search history.

(56) References Cited

U.S. PATENT DOCUMENTS 6,037,784 A    3/2000  Smith
7,135,871 B1   11/2006 Pelletier
(Continued)

FOREIGN PATENT DOCUMENTS

CN         210572076 U    5/2020
WO         2002/086459 A1  10/2002

OTHER PUBLICATIONS

International Search Report for International Application No. PCT/AU2023/050676, mailed Sep. 21, 2023, 5 pages.
(Continued)

*Primary Examiner* — Amy He
(74) *Attorney, Agent, or Firm* — TraskBritt

(57) ABSTRACT

A soil carbon sensor includes a probe body for placement into soil, a first detector supported by the probe body that transmits a frequency-modulated signal into the soil. The first detector includes a first electrode configured responsive to a moisture content and bulk density of the soil. A second detector is supported by the probe body and transmits an amplitude-modulated signal into the soil. The second detector includes a second electrode configured responsive to a soil organic carbon content of the soil. A processor is arranged in signal communication with the first and second detectors, the processor configured to generate and control the transmission of the frequency and amplitude modulated signals to monitor the first electrode to capture an impedance measurement indicative of the moisture content and bulk density, and to monitor the second electrode to capture a
(Continued)

current measurement indicative of the soil organic carbon (SOC) content.

20 Claims, 5 Drawing Sheets

(51) Int. Cl.
    *G01N 27/30*     (2006.01)
    *G01N 27/49*     (2006.01)
    *G01N 33/24*     (2006.01)

(56) References Cited

U.S. PATENT DOCUMENTS

| | | | |
|---|---|---|---|
| 11,657,903 B2 * | 5/2023 | McBratney | G06Q 10/06 702/23 |
| 2005/0067190 A1 | 3/2005 | Tabanou et al. | |
| 2010/0019772 A1 | 1/2010 | Gorek | |
| 2015/0247787 A1 * | 9/2015 | Yeomans | G01N 5/045 73/865 |

OTHER PUBLICATIONS

International Written Opinion for International Application No. PCT/AU2023/050676, mailed Sep. 21, 2023, 4 pages.
Australian Certificate of Grant for Australian Application No. 2023314142, dated Nov. 7, 2024, 41 pages.

\* cited by examiner

SOIL CARBON SENSOR AND SENSING ARRANGEMENT

CROSS-REFERENCE TO RELATED APPLICATIONS

This application is a national phase entry under 35 U.S.C. § 371 of International Patent Application PCT/AU2023/050676, filed Jul. 25, 2023, designating the United States of America and published as International Patent Publication WO 2024/020629 A1 on Feb. 1, 2024, which claims the benefit under Article 8 of the Patent Cooperation Treaty of Australian Patent Application Serial No. 2022902091, filed Jul. 26, 2022.

TECHNICAL FIELD

This disclosure broadly relates to the field of soil carbon sensing and, more particularly, to a soil carbon sensor and an associated arrangement for soil carbon sensing, as well as an associated method of soil carbon sensing.

BACKGROUND

The following discussion of the background art is intended to facilitate an understanding of only the present disclosure. The discussion is not an acknowledgement or admission that any of the material referred to is or was part of the common general knowledge as at the priority date of the application.

Soil is the most abundant terrestrial store of organic carbon. Soil carbon is the solid carbon stored in global soils. This includes both soil organic matter and inorganic carbon as carbonate minerals. Soil carbon is a carbon sink relating to the global carbon cycle, playing a role in biogeochemistry, climate change mitigation, and constructing global climate models. The majority of soil carbon is held as soil organic carbon (SOC), however soils in arid and semiarid regions also hold significant forms of soil inorganic carbon (SIC), primarily as elemental carbon and carbonate materials such as calcite, dolomite, and gypsum.

Levels of SOC are determined by interactions among dynamic ecological processes such as photosynthesis, decomposition, and soil respiration, all of which may be influenced by agricultural and farming practices. Soil organic carbon is an indicator of soil quality as it affects nutrient cycling, aggregate stability, structure, water infiltration, and soil vulnerability to erosion. Management of soil organic carbon is central to maintaining soil health, ensuring food security, and mitigating climate change. While SIC largely depends on soil type and elemental composition, SOC is more dynamic and variable.

Studies have estimated that, at scale, carbon farming could draw enough carbon out of the atmosphere to offset significant portions of annual anthropogenic carbon emissions. Given the broad recognition of the need for atmospheric carbon removal in addition to aggressive emissions reductions, carbon farming is seen as a promising climate response. Furthermore, carbon farming can result in significant agricultural and ecological benefits, such as improved soil structure, a robust soil microbiome, as well as better water retention, all of which bolster agriculture's climate change resilience.

To this end, economic imperatives and social policies can provide financial incentives to motivate widespread implementation of carbon farming practices. Farmers can participate in voluntary carbon markets, selling carbon credits that represent the soil carbon accumulated through farming practices. Government policy initiatives also reward carbon farming through subsidy or grant programs. Similarly, consumers could support "low-carbon" or "carbon-neutral" products through their purchasing decisions.

For example, under a carbon trading system, farmers and landowners are paid for adopting carbon-sequestration techniques, provided their increases in carbon can be measured, monitored and verified. Accounting for soil carbon changes has historically been difficult, as carbon increases due to farming practice changes are very small, and carbon content varies widely within a field, even over a few meters. Also, the composition and persistence of different types of soil organic carbon varies. In addition to the macro factors such as soil formation, soil type, and historical land use, there are many micro factor influences, including crop residues that are distributed unevenly from combine harvesters, heavy rains that remove and deposit piles of residue sporadically, animals that may defecate and die in random locations, and many other factors that add variations and dynamicity to accurate and meaningful SOC sensing.

Accordingly, the difficulty of getting standardized, comprehensive, and accurate SOC measurements presents a major impediment to the wider development of such policies and programs. Traditional soil carbon monitoring techniques are slow and invasive, and generally require extracting soil cores that are shipped to a lab, where they are analyzed using expensive analytical chemistry methods, such as dry combustion or the Walkley-Black chromic acid wet oxidation method. Such conventional soil carbon measurement approaches are expensive and can take days or weeks and currently makes it impractical to run soil carbon incentive initiatives at scale.

To date, more practical developments for measuring soil carbon concentrations have been focused on visible-near-infrared (vis-NIR) spectroscopy and, for bulk density, active gamma-ray attenuation. Further developments have also considered laser-induced breakdown spectroscopy (LIBS) to generate a high-temperature plasma on the surface of collected soil samples, where a resulting emission spectrum can be analyzed using a spectrometer to identify the elemental composition of the soil. Such recent developments for measuring soil organic carbon concentrations present significant shortcomings, including reliability, accuracy, precision and cost. Since NIR spectroscopy, LIBS and related optical methods require an optical input to probe soil composition, the depth of sampling/testing is very limited, in general.

Accordingly, Applicant has identified a need in the art for accurate and cost-efficient means for long-term in-situ measuring and monitoring of soil carbon content for monitoring overall soil health for farming and industrial practices, as well as enabling accurate measurement of soil carbon content towards carbon management policies and programs.

The current disclosure was conceived with this goal in mind.

BRIEF SUMMARY

The skilled addressee is to appreciate that the present disclosure makes reference to specific arrangements and methodologies for sensing of soil carbon; however, other constituent elements or parts of soil may be sensed in a similar manner, as per arbitrary requirements. For example, nitrogen, pH, nutrients, organic matter(s) and related pedogenesis parent materials may be sensed in a similar manner. Accordingly, while reference herein is made to carbon sensing, such reference is made in a non-exhaustive manner with suitable alteration apposite for sensing of other soil elements, as appropriate and generally within the understanding of the skilled addressee.

According to one embodiment of the disclosure, a soil carbon sensor is disclosed, comprising:
- a probe body configured for operative placement into soil;
- a first detector supported by the probe body and configured to transmit a frequency-modulated signal into the soil, the first detector including a first electrode configured responsive to a moisture content and bulk density of the soil;
- a second detector supported by the probe body and configured to transmit an amplitude-modulated signal into the soil, the second detector including a second electrode configured responsive to a soil organic carbon (SOC) content of the soil; and
- a processor arranged in signal communication with the first and second detectors, the processor configured to:
  i. generate and control the transmission of the frequency and amplitude modulated signals;
  ii. monitor the first electrode to capture an impedance measurement indicative of the moisture content and bulk density; and
  iii. monitor the second electrode to capture a current measurement indicative of the soil organic carbon (SOC) content;
- wherein such captured impedance and current measurements are useable to calculate a carbon content of the soil.

In an embodiment, the soil carbon sensor comprises a transmitter arranged in signal communication with the processor, which is configured to transmit the captured impedance and current measurements to a remote computer system for processing.

In an embodiment, the soil carbon sensor comprises an energy source configured to supply the processor and detectors with electrical energy.

In an embodiment, the energy source comprises an electrochemical cell or capacitor, with or without a photovoltaic cell for charging the cell or capacitor.

In an embodiment, the energy source is unitary with the probe body, or the energy source is modular.

In an embodiment, the probe body is configured for placement into soil by comprising a stake-like elongate form to facilitate insertion of the body into soil.

In an embodiment, the first electrode is configured responsive to the moisture content and bulk density of the soil by comprising a two-electrode configuration with an ionic coating or film.

In an embodiment, the two-electrode configuration comprises a working electrode of gold and a reference electrode of silver and/or silver chloride.

In an embodiment, the ionic coating or film of the two-electrode configuration comprises 1-butyl-3-methylimidazoliumtrifluoromethanesulfonate (BMIM OTf).

In an embodiment, the ionic coating or film of the two-electrode configuration includes a protective coating, such as a sulfonated tetrafluoroethylene-based ionomer copolymer.

In an embodiment, the second electrode is configured responsive to the soil organic carbon (SOC) content of the soil by comprising a three-electrode configuration with an ionic coating or film.

In an embodiment, the three-electrode configuration comprises a working electrode of gold, a counter electrode of carbon, and a reference electrode of silver and/or silver chloride.

In an embodiment, the ionic coating or film of the three-electrode configuration comprises a mixture of 1-Butyl-3-methylimidazolium tetrafluoroborate (BMIM BF4), a sulfonated tetrafluoroethylene-based copolymer ionomer, carbon particles and a cross-linked polymethylmethacrylate resin.

In an embodiment, ionic coating or film of the three-electrode configuration includes a protective coating, such as a sulfonated tetrafluoroethylene-based ionomer copolymer.

In an embodiment, the processor generates and transmits the frequency-modulated signal via the first detector as an alternating current (AC) bias in a range of 1 mV to 100 mV applied with frequency sweep of 100 Hz to 1 MHz, the processor monitoring the first electrode to capture the impedance measurement indicative of the moisture content and bulk density.

In an embodiment, the processor generates and transmits the amplitude-modulated signal via the second detector as a squarewave voltammetry process where a square wave is pulsed with a voltage bias having a step size between 3 mV to 8 mV, a pulse size of between 15 mV to 45 mV, with a frequency between 10 Hz to 50 Hz is swept over a voltage range of between 0 V to 2 V, the processor monitoring the second electrode to capture the current measurement indicative of the SOC content.

In an embodiment, the soil carbon sensor comprises a pH sensor via which the processor is configurable to measure a pH value of the soil.

In an embodiment, the processor is configured to account for a measured soil pH value during subsequent calculation of a carbon content of the soil.

In an embodiment, the soil carbon sensor comprises a fluid deployment assembly configured to deploy a suitable fluid proximate an electrode to facilitate formation of an electrolyte solution with the soil.

In an embodiment, the soil carbon sensor comprises a fluid deployment assembly configured to deploy a suitable fluid proximate an electrode to affect a pH value of the soil.

In an embodiment, the fluid deployment assembly comprises a fluid reservoir arranged in fluid communication with an ejector arranged proximate an electrode, the ejector operatively controlled by the processor.

In an embodiment, the processor is configured to actuate the ejector to eject a predetermined amount of fluid proximate the electrode.

In an embodiment, the processor is configured to actuate the ejector to establish a predetermined soil moisture content via the first detector.

In an embodiment, the soil carbon sensor comprises an electrode cover configured controllably to cover an electrode.

In an embodiment, the electrode cover is slidably arranged on the probe body and includes an actuator controlled by the processor in order to cover or uncover an electrode.

Typically, the processor comprises any suitable processor or microcontroller configured to receive input, perform logical and arithmetical operations on a suitable instruction set, and provide output, as well as transitory and/or non-transitory electronic storage.

According to another embodiment of the disclosure, a soil carbon sensing arrangement is disclosed, comprising:

a plurality of soil carbon sensors in accordance with the first embodiment of the disclosure, the sensors installed in a field;

a base station configured to receive captured impedance and current measurements from each soil carbon sensor, the base station configured to transmit such measurements; and a remote processing system configured to receive such current and impedance measurements and to calculate a carbon content of the field according to such received impedance and current measurements.

According to another embodiment of the disclosure, a method for soil carbon sensing is disclosed, the method comprising the steps of:

transmitting a frequency-modulated signal into soil via a first detector having a first electrode configured responsive to moisture content and bulk density of the soil;

transmitting an amplitude-modulated signal into the soil via a second detector having a second electrode configured responsive to a soil organic carbon (SOC);

monitoring, by means of a processor arranged in signal communication with the first and second detectors, the first electrode to capture an impedance measurement indicative of the moisture content and bulk density, and the second electrode to capture a current measurement indicative of the soil organic carbon (SOC); and calculating a carbon content of the soil according to such captured impedance and current measurements.

In an embodiment, the first electrode is configured responsive to the moisture content and bulk density of soil by comprising a two-electrode configuration with an ionic coating or film.

In an embodiment, the two-electrode configuration comprises a working electrode of gold and a reference electrode of silver and/or silver chloride.

In an embodiment, the ionic coating or film of the two-electrode configuration comprises 1-butyl-3-methylimidazoliumtrifluoromethanesulfonate (BMIM OTf).

In an embodiment, the ionic coating or film of the two-electrode configuration includes a protective coating, such as a sulfonated tetrafluoroethylene-based ionomer copolymer.

In an embodiment, the second electrode is configured responsive to the soil organic carbon (SOC) content of the soil by comprising a three-electrode configuration with an ionic coating or film.

In an embodiment, the three-electrode configuration comprises a working electrode of gold, a counter electrode of carbon, and a reference electrode of silver and/or silver chloride.

In an embodiment, the ionic coating or film of the three-electrode configuration comprises a mixture of 1-butyl-3-methylimidazolium tetrafluoroborate (BMIM BF4), a sulfonated tetrafluoroethylene-based ionomer copolymer, carbon particles and a cross-linked polymethylmethacrylate resin.

In an embodiment, ionic coating or film of the three-electrode configuration includes a protective coating, such as a sulfonated tetrafluoroethylene-based ionomer copolymer.

In an embodiment, the step of transmitting the frequency-modulated signal comprises transmitting an alternating current (AC) bias in a range of 1 mV to 100 mV applied with frequency sweep of 100 Hz to 1 MHz.

In an embodiment, the step of transmitting the amplitude-modulated signal comprises a squarewave voltammetry process where a square wave is pulsed with a voltage bias having a step size between 3 mV to 8 mV, a pulse size of between 15 mV to 45 mV, with a frequency between 10 Hz to 50 Hz is swept over a voltage range of between 0 V to 2 V.

In an embodiment, method includes a step of deploying a fluid via a fluid deployment assembly proximate an electrode to facilitate formation of an electrolyte solution with the soil.

In an embodiment, method includes a step of deploying a fluid via a fluid deployment assembly proximate an electrode to affect a pH value of the soil.

In an embodiment, the fluid deployment assembly comprises a fluid reservoir arranged in fluid communication with an ejector arranged proximate an electrode, the ejector operatively controlled by the processor.

In an embodiment, the step of deploying fluid comprises actuating the ejector, via the processor, to eject a predetermined amount of fluid proximate the electrode.

In an embodiment, method includes a step covering or uncovering an electrode, by means of an electrode cover controlled by the processor, to separate the electrode from the soil.

According to yet another embodiment of the disclosure, a soil carbon sensor, a soil carbon sensing arrangement and a method for soil carbon sensing are disclosed, substantially as herein described and/or illustrated.

BRIEF DESCRIPTION OF THE DRAWINGS

The description will be made with reference to the accompanying drawings in which.

DETAILED DESCRIPTION

Figure 1:
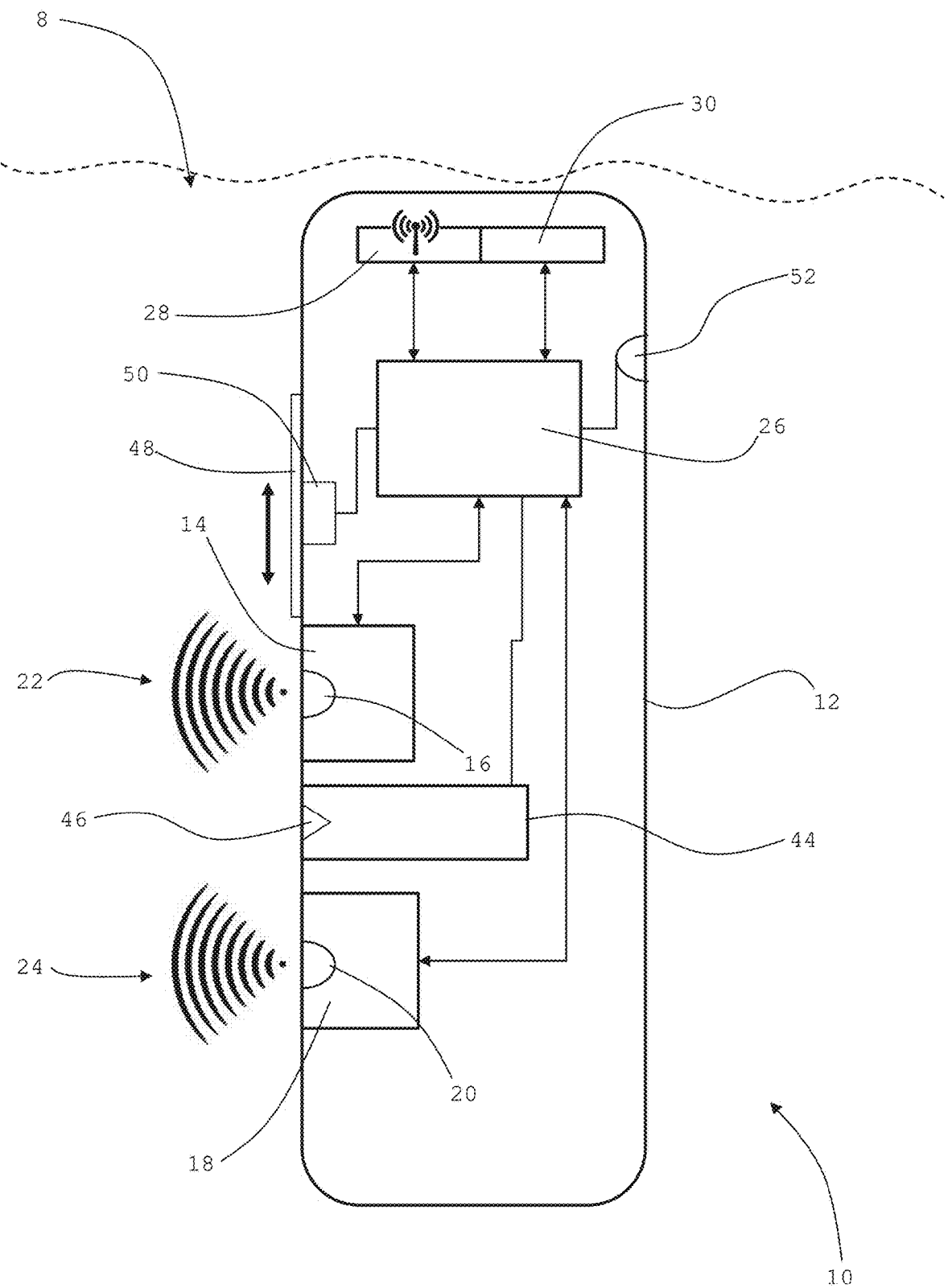
FIG. 1 is a diagrammatic overview representation of a broad embodiment of a soil carbon sensor, in accordance with aspects of the present disclosure.

Further features of the present disclosure are more fully described in the following description of several non-limiting embodiments thereof. This description is included solely for the purposes of exemplifying the present disclosure to the skilled addressee. It should not be understood as a restriction on the broad summary or description of the disclosure as set out above.

In the figures, incorporated to illustrate features of the example embodiment or embodiments, like reference numerals are used to identify like parts throughout. Additionally, features, mechanisms and aspects well-known and understood in the art will not be described in detail, as such features, mechanisms and aspects will be within the understanding of the skilled addressee.

Broadly, the present disclosure describes automatable means and techniques whereby soil carbon content, particularly soil organic carbon (SOC) is measurable in a timely and inexpensive manner, as compared to conventional practices. Such soil carbon measurements are economically and practically scalable and may facilitate ongoing monitoring of soil carbon content for monitoring overall soil health for farming practices, as well as enabling accurate measurement of soil carbon content towards carbon management policies and programs.

With reference now to the accompanying figures, there is broadly exemplified a soil carbon sensor 10 (also referred to herein as sensor 10) that generally comprises a probe body 12, a first detector 14, a second detector 18, and a processor 26. The probe body 12 is generally inserted into soil 8 in which carbon sensing is desired. The probe body 12 may be inserted at a specific depth and/or orientation into the soil 8, and the probe body 12 is typically, but not necessarily, configured for placement into soil 8 by comprising a stake-like elongate form to facilitate insertion of the body into soil. Of course, variations on the probe body 12 are possible and expected, e.g., the first and second detectors 14 and 18 housed in separate but associated housings, or the like.

Figure 2:
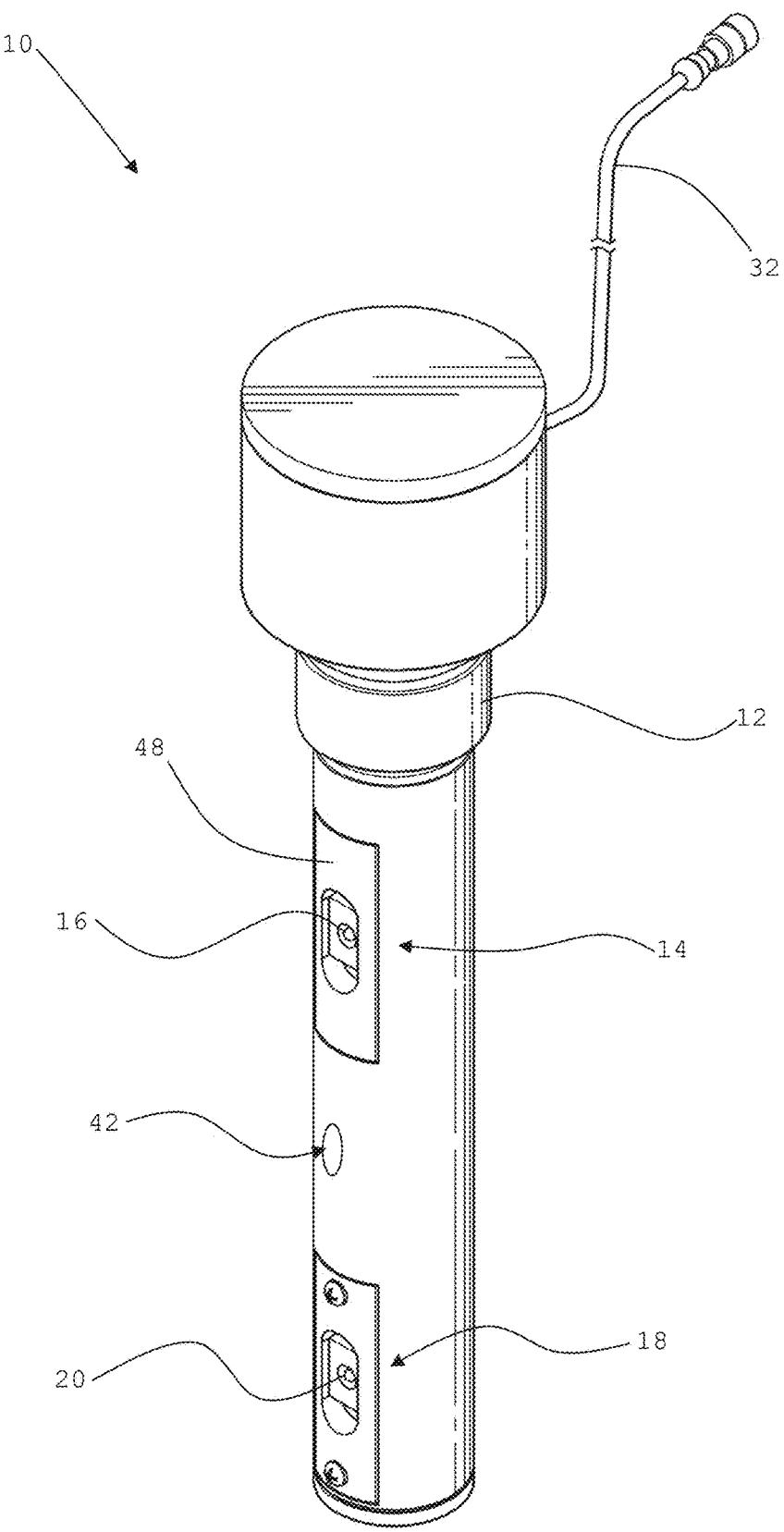
FIG. 2 is a diagrammatic perspective-view representation of an example of a soil carbon sensor.
Figure 3:
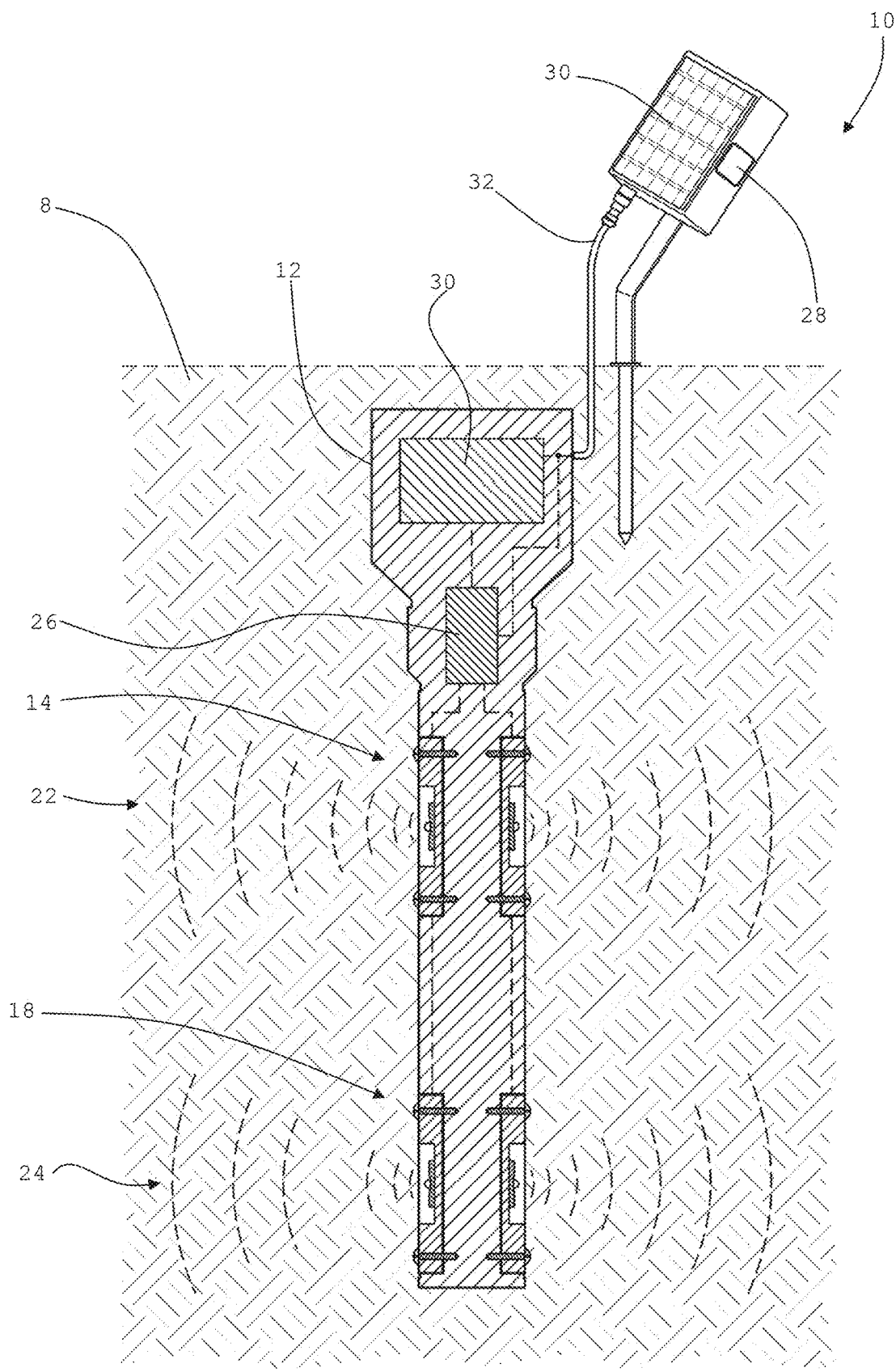
FIG. 3 is diagrammatic in-situ representation of the soil carbon sensor of FIG. 2 installed in soil.

The sensor 10 also typically includes an energy source 30 that is configured to supply the processor 26 and detectors 14 and 18 with electrical energy. In one embodiment, the energy source 30 may comprise an electrochemical cell, e.g., a battery, or a capacitor, i.e., supercapacitor, and may also include a photovoltaic cell for charging the cell or capacitor. In one embodiment, the energy source 30 is unitary with the probe body 12, but other embodiments may see the energy source 30 being modular to facilitate ease of access and/or replacement. For example, in the embodiment of FIGS. 2 to 4, the sensor 10 comprises a separate or modular photovoltaic cell that is locatable above-ground in order to provide electrical energy to a suitable battery inside the probe body 12.

In an embodiment, the soil carbon sensor 10 typically comprises a transmitter 28, which is arranged in signal communication with the processor 26 and which is configured to transmit information to a remote computer system 38 for further processing. In a typical embodiment, the transmitter 28 is also located above-ground and incorporated into the modular photovoltaic cell to facilitate transmission of information from the in-ground sensor 10. Such transmitted information typically comprises captured impedance and current measurements, as described in more detail below. Of course, variations on the above are possible and expected and within the scope of the present disclosure.

The skilled addressee will appreciate that the transmitter 28 may form part of a transceiver and that the processor 26 may be configured to receive instructions and/or updates from the remote computer system 38. Such instructions may include polling requests for transmitted information, firmware updates, and/or the like. The transmission between the sensor 10 and remote computer system 38 may also be compressed and/or encrypted.

The processor 26 may comprise any suitable processor or microcontroller configured to receive input, perform logical and arithmetical operations on a suitable instruction set, and provide output, as well as transitory and/or non-transitory electronic storage.

The sensor 10 typically includes the first detector 14 supported by the probe body 12 and is operatively configured to transmit a frequency-modulated signal 22 into the soil 8. As will be appreciated by the skilled addressee, such a signal generally comprises an electromagnetic signal as understood in the field of electrical and electronic engineering. The first detector 14 includes a first electrode 16 that is configured to be responsive to a moisture content and bulk density of the soil 8, as described in more detail below.

In one embodiment, the first electrode 16 is configured to be responsive to the moisture content and bulk density of the soil 8 by comprising a two-electrode configuration with an ionic coating or film applied thereto. For example, Applicant has found that screen-printed electrodes (SPEs) from the Metrohm™ Dropsens™ line are useful for this application, but of course variations are possible and expected. In one embodiment, the two-electrode configuration of the first detector 14 comprises a working electrode of gold and a reference electrode of silver and/or silver chloride. In an embodiment, the ionic coating or film of the two-electrode configuration comprises 1-butyl-3-methylimidazoliumtrifluoromethanesulfonate (BMIM OTf). Such an ionomer coating or film of the two-electrode configuration may also include a protective and/or conductive coating, such as a sulfonated tetrafluoroethylene-based ionomer copolymer, or the like.

The sensor 10 further includes the second detector 18 that is typically supported by the probe body 12 and that is operatively configured to transmit an amplitude-modulated signal 24 into the soil 8. The second detector 18 generally comprises a second electrode 20 that is configured to be responsive to a soil organic carbon (SOC) content of the soil 8, as described in more detail below.

In an embodiment, second electrode 20 is configured to be responsive to the soil organic carbon (SOC) content of the soil 8 by comprising a three-electrode configuration with an ionic coating or film applied thereto. Again, screen-printed electrodes (SPEs) from the Metrohm™ Dropsens™ line may be useful for this application. In one embodiment, the three-electrode configuration of second electrode 20 comprises a working electrode of gold, a counter electrode of carbon, typically carbon paste, and a reference electrode of silver and/or silver chloride.

In one embodiment, the ionic coating or film of the three-electrode configuration of second electrode 20 comprises a mixture of 1-butyl-3-methylimidazolium tetrafluoroborate (BMIM BF4), a sulfonated tetrafluoroethylene-based ionomer copolymer, carbon particles, such as biochar, and a polymethylmethacrylate resin. In an embodiment, the ionic coating or film of the three-electrode configuration also includes a protective and/or conductive coating, such as a sulfonated tetrafluoroethylene-based ionomer copolymer, or the like.

Accordingly, as described herein, a fundamental operating principle of the soil carbon sensor 10 of the present disclosure comprises the mechanism of organic carbon pools in soil matrices, i.e., SOC, interacting with the detectors 14 and 18 described herein, having such electrode configurations that are excited at a specific potential, causing corresponding electrochemical signals obtained as a function of interfacial activity at the electrodes 16 and 20. Such electrochemical signals may provide an input into a pre-configured model, typically based on calibration curves of soils with known composition, moisture level and pH, to determine an overall SOC quantification for the soil 8.

Specifically, as described above, the electrodes 16 and 20 are functionalized with particular ion surface treatments or coatings that interact chemically with target analytes in the soil 8 when a bias is applied in accordance with aspects of the disclosure. These interactions are then transduced to an electrical output that varies from a baseline due to modulation of the electrochemical signal parameters at the interface. The resulting output can then be utilized to calculate SOC at accuracy and precision comparable with conventional lab-based methods.

The skilled addressee is to appreciate that variations on such ionic surface treatments or coatings are expected and anticipated. For example, some non-limiting examples of suitable cations for the electrochemical processes described herein may be selectable from a group consisting of imidazolium, pyrolidinium and tetraalkyl amines with a combination of methyl, ethyl, propyl, butyl, pentyl groups. Similarly, apposite anions may be selectable from a non-exhaustive group consisting of tetrafluoroborate (BF4), hexafluorophosphate (PF6), bis-trifluoromethanesulfonimide (NTf2), trifluoromethanesulfonate (OTf), dicyanamide (N(CN)2), hydrogen sulphate (HSO4), and ethyl sulphate (EtOSO3). Again, variations hereon are possible and anticipated.

For example, non-limiting examples of ionic surface treatments or coatings may be selectable from a group consisting of 1-butyl-3-methylimidazolium trifluoromethanesulfonate; 1-butyl-3-methylimidazolium bis(trifluoromethyl) sulfonyl) imide; 1-butyl-3-methylimidazolium hexafluorophosphate; 1-butyl-3-methylimidazolium bis(trifluoromethyl) sulfonyl) amide; 1-butyl-3-methylimidazolium tetrafluoroborate; 1-Butyl-2,3-dimethylimidazolium trifluoromethane Sulfonate; 1-Butyl-2,3-dimethylimidazolium bis(trifluoromethyl) sulfonyl)imide; 1-Butyl-2,3-dimethylimidazolium hexafluorophosphate; 1-Butyl-2,3-dimethylimidazolium bis(trifluoromethyl) sulfonyl)amide; 1-Butyl-2,3-dimethylimidazolium tetrafluoroborate; 1-butyl-1-methylpyrrolidinium trifluoromethanesulfonate; 1-butyl-1-methylpyrrolidinium bis(trifluoromethyl) sulfonyl)imide; 1-butyl-1-methylpyrrolidinium hexafluorophosphate; 1-butyl-1-methylpyrrolidinium bis(trifluoromethyl) sulfonyl)amide; 1-butyl-1-methylpyrrolium tetrafluoroborate; 1-butyl-methylpyridinium trifluoromethanesulfonate; 1-butyl-1-methylpyridinium bis(trifluoromethyl) sulfonyl); 1-butyl-1-methylpyridinium hexafluorophosphate; 1-butyl-1-methylpyridinium bis(trifluoromethyl) sulfonyl)amide; 1-butyl-1-methylpyridinium tetrafluoroborate; 1-Ethyl-1-methylpyrrolidinium trifluoromethanesulfonate; 1-Ethyl-1-methylpyrrolidinium bis(trifluoromethyl) sulfonyl)imide; 1-Ethyl-1-methylpyrrolidinium hexafluorophosphate; 1-Ethyl-1-methylpyrrolidinium bis(trifluoromethyl) sulfonyl)amide; 1-Ethyl-1-methylpyrrolidinium tetrafluoroborate; 1-Ethyl-3-methylimidazolium trifluoromethanesulfonate; 1-Ethyl-3-methylimidazolium bis(trifluoromethyl) sulfonyl)imide; 1-Ethyl-3-methylimidazolium hexafluorophosphate; 1-Ethyl-3-methylimidazolium bis(trifluoromethyl) sulfonyl)amide; 1-Ethyl-3-methylimidazolium tetrafluoroborate; 1-methyl-1-propylpyrroldinium trifluoromethanesulfonate; 1-methyl-1-propylpyrroldinium 1-methyl-1-propylpyrroldinium bis(trifluoromethyl) sulfonyl)imide; bis(trifluoromethylsulfonyl)amide; 1-methyl-1-propylpyrroldinium hexafluorophosphate; and 1-methyl-1-propylpyrroldinium tetrafluoroborate. Of course, variations hereon are also possible and expected without departing from the scope of the present disclosure.

The carbon sensor 10 generally includes the processor 26 that is arranged in signal communication with the first and second detectors 14 and 18, with the processor 26 configured to generate and control the transmission of the frequency- and amplitude-modulated signals 22 and 24, as well as to monitor the first electrode 16 to capture an impedance measurement indicative of the moisture content and bulk density of the soil 8, and to monitor the second electrode 20 to capture a current measurement indicative of the soil organic carbon (SOC) content of the soil 8. In this manner, such captured impedance and current measurements are useable to calculate a carbon content of the soil.

In one embodiment, the processor 26 generates and transmits the frequency-modulated signal 22 via the first detector 14 as an alternating current (AC) bias in a range of 1 mV to 100 mV applied with frequency sweep of 100 Hz to 1 MHZ, the processor 26 monitoring the first electrode 16 to capture the impedance measurement indicative of the moisture content and bulk density, i.e., perform impedance spectroscopy.

In one embodiment, the processor 26 generates and transmits the amplitude-modulated signal 24 via the second detector 18 as a squarewave voltammetry process, i.e., functioning as a potentiostat. As known in the art, voltammetry is an electroanalytical method where information about an analyte, such as the soil 8, is obtainable by measuring current as the potential is varied. The analytical data for a voltametric process generally comes in the form of a voltammogram, which plots the current produced by the analyte versus the potential of the working electrode relative to the reference electrode.

In a squarewave voltametric process, the current at a working electrode is generally measured while the potential between the working electrode and a reference electrode is pulsed forward and backward at a predetermined frequency. A potential waveform can be viewed as a superposition of a regular squarewave onto an underlying staircase waveform. Current is typically sampled at two intervals, i.e., once at the end of the forward potential pulse and again at the end of the reverse potential pulse (in both cases immediately before the potential direction is reversed). As a result of this current sampling technique, the contribution to the current signal resulting from capacitive or non-faradaic current is minimal.

In one embodiment, the processor 26 is configured to generate a square wave that is pulsed with a voltage bias having a step size between 3 mV to 8 mV, a pulse size of between 15 mV to 45 mV, with a frequency between 10 Hz to 50 Hz swept over a voltage range of between 0 V to 2 V. Of course, variations hereon are possible and expected. The processor 26 is also configured to monitor the second electrode 20 to capture the current measurement indicative of the SOC content.

In one embodiment, the soil carbon sensor 10 also comprises a pH sensor 52 via which the processor 26 is configurable to measure a pH value of the soil 8. In one embodiment, the processor 26 may be configured to account for such a measured soil pH value during subsequent calculation of a carbon content of the soil.

In one embodiment, the soil carbon sensor 10 further comprises a fluid deployment assembly 42 that is broadly configured to deploy a suitable fluid proximate an electrode 16 and/or 20 in order to facilitate formation of an electrolyte solution with the soil 8. In one embodiment, the fluid deployment assembly 42 comprises a fluid reservoir 44 that is arranged in fluid communication with a suitable fluid ejector 46 arranged proximate an electrode 16 and/or 20. The ejector 46 is operatively controlled by the processor 26. The fluid may comprise any desired fluid, such as deionised or distilled water, a particular electrolyte, a gas, or the like. The skilled addressee is to appreciate that such fluid may be selected to facilitate the squarewave voltammetry process and/or similar electrochemistry performed by the sensor 10.

Similarly, in one embodiment, the soil carbon sensor 10 may also comprise a fluid deployment assembly 42 that is configured to deploy a suitable fluid proximate an electrode to affect a pH value of the soil 8. For example, such a fluid deployment assembly 42 may be used to adjust a soil pH to affect the solubility of humic/fulvic acids within an electrolyte forming part of an electrochemistry measurement made by the sensor 10, or the like. Similarly, the fluid deployment assembly 42 may be configured to calibrate the pH sensor 52, or the like.

In one embodiment, the processor 26 is configured to actuate the ejector 46 to eject a predetermined amount of fluid proximate the electrode, e.g., a specific volume of fluid. Alternatively, or additionally, in one embodiment the processor 26 may be configured to actuate the ejector 46 to establish a predetermined soil moisture content via the first detector, i.e., deploy fluid until a desired soil moisture content is reached, or the like.

In one embodiment, the soil carbon sensor 10 may further comprise an electrode cover 48 that is controllably configured to cover an electrode 16 and/or 20. For example, in one embodiment the electrode cover 48 is slidably arranged on the probe body 12 and includes an actuator 50 that is controlled by the processor 26 in order to cover or uncover an electrode as required. The actuator 50 may comprise any suitable actuator, such as an electromechanical actuator, or the like. In this manner, the electrode 16 and/or 20 may be selectively covered until a measurement is taken, to protect the electrode 16 and/or 20 in-between measurements, and/or the like.

Figure 4:
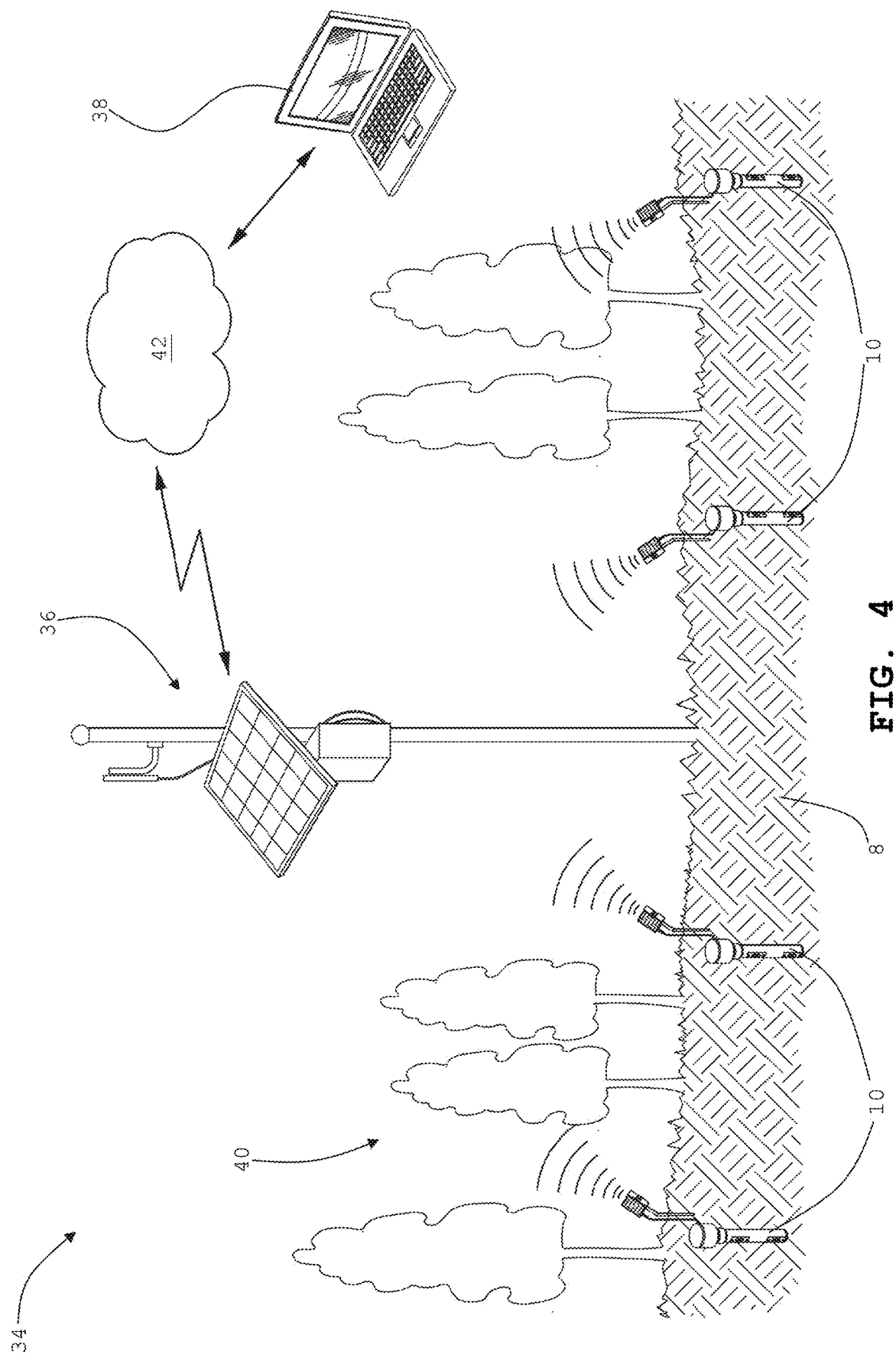
FIG. 4 is a diagrammatic overview representation of a soil carbon sensing arrangement, in accordance with aspects of the present disclosure.

With reference now to FIG. 4 of the accompanying drawings, in light of the above-described sensor 10, the present disclosure also provides for an associated soil carbon sensing arrangement 34. Such an arrangement 34 generally comprises one or more of the soil carbon sensors 10, as described above, with the sensors 10 installed in a field 40, along with a base station 36 that is configured to receive captured impedance and current measurements from each soil carbon sensor 10. The base station 36 is typically configured to transmit such measurements to a remote computer system 38 that is configured to receive such current and impedance measurements and to calculate a carbon content of the soil in the field 40 according to such received impedance and current measurements.

Figure 5:
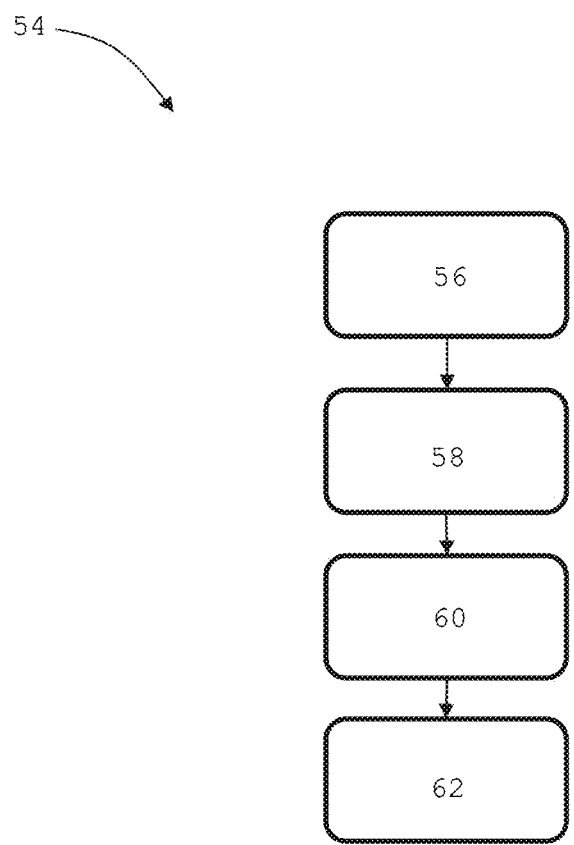
FIG. 5 is a functional block diagrammatic representation of method steps for a method for soil carbon sensing, in accordance with an aspect of the present disclosure.

Similarly, with reference to FIG. 5 of the accompanying drawings, the present disclosure further includes an associated method 54 for soil carbon sensing. Such a method 54 broadly comprises the step of transmitting 56 the frequency-modulated signal 22 into soil 8 via first detector 14 having the first electrode 16 configured responsive to the moisture content and bulk density of the soil, as well as the step of transmitting 58 the amplitude-modulated signal 24 into the soil 8 via the second detector 18 having the second electrode 20 configured responsive to soil organic carbon (SOC).

The method 54 further generally includes the steps of monitoring 60, by means of processor 26 arranged in signal communication with the first and second detectors 14 and 18, the first electrode 16 to capture the impedance measurement indicative of the moisture content and bulk density, and the second electrode 20 to capture the current measurement indicative of the soil organic carbon (SOC), as well as calculating 62 a carbon content of the soil according to such captured impedance and current measurements. Typically, the step of calculating 62 is performed via remote computer system 38, once the captured measurements are transmitted thereto via base station 36.

Applicant believes it particularly advantageous that the present disclosure provides for means for capturing measurements from soil whereby soil carbon content may be calculable. The disclosure provides for conjunctively applied direct current (DC) and alternating current (AC) based electrochemical techniques to facilitate modelling and tracking of soil organic carbon levels based on the soil's charge transfer and charge modulation capacities. Sensor 10 makes use of voltammetry and electrochemical impedance spectroscopy (EIS) techniques to survey soil organic carbon parameters from different perspectives that can then be converged to determine SOC levels based on mathematical evaluation models. In this manner, measurements of SOC and SIC are possible in a quick, automatable and timeous manner with accuracy and precision comparable with conventional lab-based methods. Sensor 10 also uses signals 22 and 24 that provide increased soil penetration when compared with conventional optical methods, such as visible-near-infrared (vis-NIR) spectroscopy and laser-induced breakdown spectroscopy (LIBS).

Optional embodiments of the present disclosure may also be said to broadly consist in the parts, elements and features referred to or indicated herein, individually or collectively, in any or all combinations of two or more of the parts, elements or features, and wherein specific integers are mentioned herein that have known equivalents in the art to which the disclosure relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a," "an," "said," "the," and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. As used herein, the term "and/or" includes any and all combinations of one or more of the associated listed items. No language in the specification should be construed as indicating any non-claimed subject matter as essential to the practice of the claimed subject matter.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It is to be appreciated that reference to "one example" or "an example" of the disclosure, or similar exemplary language (e.g., "such as") herein, is not made in an exclusive sense. Accordingly, one example may exemplify certain aspects of the disclosure, while other aspects are exemplified in a different example. These examples are intended to assist the skilled person in performing the disclosure and are not intended to limit the overall scope of the disclosure in any way unless the context clearly indicates otherwise. Variations (e.g., modifications and/or enhancements) of one or more embodiments described herein might become apparent to those of ordinary skill in the art upon reading this application. It is expected that skilled artisans will employ such variations as appropriate, and it is also intended for the claimed subject matter to be practiced other than as specifically described herein.

Any method steps, processes, and operations described herein are not to be construed as necessarily requiring their performance in the particular order discussed or illustrated, unless specifically identified as an order of performance. It is also to be understood that additional or alternative steps may be employed.

The invention claimed is:

1. A soil carbon sensor comprising:
a probe body configured for operative placement into soil;
a first detector supported by the probe body and configured to transmit a frequency-modulated signal into the soil, the first detector including a first electrode configured responsive to a moisture content and bulk density of the soil;
a second detector supported by the probe body and configured to transmit an amplitude-modulated signal into the soil, the second detector including a second electrode configured responsive to a soil organic carbon (SOC) content of the soil; and
a processor arranged in signal communication with the first and second detectors, the processor configured to:
  i. generate and control the transmission of the frequency amplitude-modulated signals;
  ii. monitor the first electrode to capture an impedance measurement indicative of the moisture content and bulk density; and
  iii. monitor the second electrode to capture a current measurement indicative of the soil organic carbon (SOC) content;
wherein such captured impedance and current measurements are useable to calculate a carbon content of the soil.

2. The sensor of claim 1, wherein the first electrode is configured responsive to the moisture content and bulk density of the soil by comprising a two-electrode configuration with an ionic coating or film.

3. The sensor of claim 2, wherein the ionic coating or film of the two-electrode configuration comprises 1-Butyl-3-methylimidazoliumtrifluoromethanesulfonate (BMIM OTf).

4. The sensor of claim 2, wherein the ionic coating or film of the two-electrode configuration includes a protective coating, such as a sulfonated tetrafluoroethylene-based ionomer copolymer.

5. The sensor of claim 1, wherein the second electrode is configured responsive to the soil organic carbon (SOC) content of the soil by comprising a three-electrode configuration with an ionic coating or film.

6. The sensor of claim 5, wherein the ionic coating or film of the three-electrode configuration comprises a mixture of 1-Butyl-3-methylimidazolium tetrafluoroborate (BMIM BF4), a sulfonated tetrafluoroethylene-based ionomer copolymer, carbon particles and a cross-linked polymethylmethacrylate resin.

7. The sensor of claim 6, wherein the ionic coating or film of the three-electrode configuration includes a protective coating, such as a sulfonated tetrafluoroethylene-based ionomer copolymer.

8. The sensor of claim 1, wherein the processor generates and transmits the frequency-modulated signal via the first detector as an alternating current (AC) bias in a range of 1 mV to 100 mV applied with frequency sweep of 100 Hz to 1 MHz, the processor monitoring the first electrode to capture the impedance measurement indicative of the moisture content and bulk density.

9. The sensor of claim 1, wherein the processor generates and transmits the amplitude-modulated signal via the second detector as a squarewave voltammetry process where a square wave is pulsed with a voltage bias having a step size between 3 mV to 8 mV, a pulse size of between 15 mV to 45 mV, with a frequency between 10 Hz to 50 Hz is swept over a voltage range of between 0 V to 2 V, the processor monitoring the second electrode to capture the current measurement indicative of the SOC content.

10. The sensor of claim 1, further comprising a pH sensor via which the processor is configurable to measure a pH value of the soil.

11. The sensor of claim 1, further comprising a fluid deployment assembly configured to deploy a suitable fluid proximate an electrode to affect a pH value of the soil.

12. The sensor of claim 1, further comprising a fluid deployment assembly configured to deploy a suitable fluid proximate an electrode to facilitate formation of an electrolyte solution with the soil.

13. A soil carbon sensing arrangement comprising:
a plurality of soil carbon sensors in accordance with claim 1, the plurality of soil carbon sensors installed in a field with each sensor comprising a transmitter arranged in signal communication with the processor, which is configured to transmit captured impedance and current measurements;
a base station configured to receive such captured impedance and current measurements from each soil carbon sensor, the base station configured to transmit such measurements; and
a remote processing system configured to receive such current and impedance measurements and to calculate a carbon content of the field according to such received impedance and current measurements.

14. A method for soil carbon sensing, the method comprising the steps of:
transmitting a frequency-modulated signal into soil via a first detector having a first electrode configured responsive to moisture content and bulk density of the soil;
transmitting an amplitude-modulated signal into the soil via a second detector having a second electrode configured responsive to a soil organic carbon (SOC);
monitoring, by means of a processor arranged in signal communication with the first and second detectors, the first electrode to capture an impedance measurement indicative of the moisture content and bulk density, and the second electrode to capture a current measurement indicative of the soil organic carbon (SOC); and
calculating a carbon content of the soil according to such captured impedance and current measurements.

15. The method of claim 14, wherein the first electrode is configured responsive to the moisture content and bulk density of soil by comprising a two-electrode configuration with an ionic coating or film.

16. The method of claim 15, wherein the ionic coating or film of the two-electrode configuration comprises 1-Butyl-3-methylimidazoliumtrifluoromethanesulfonate (BMIM OTf).

17. The method of claim 16, wherein the ionic coating or film of the two-electrode configuration includes a protective coating, such as a sulfonated tetrafluoroethylene-based ionomer copolymer.

18. The method of claim 14, wherein the second electrode is configured responsive to the soil organic carbon (SOC) content of the soil by comprising a three-electrode configuration with an ionic coating or film.

19. The method of claim 18, wherein the ionic coating or film of the three-electrode configuration comprises a mixture of 1-Butyl-3-methylimidazolium tetrafluoroborate (BMIM BF4), a sulfonated tetrafluoroethylene-based ionomer copolymer, carbon particles and a polymethylmethacrylate resin.

20. The method of claim 14, wherein the step of transmitting the frequency-modulated signal comprises transmitting an alternating current (AC) bias in a range of 1 mV to 100 mV applied with frequency sweep of 100 Hz to 1 MHz and wherein the step of transmitting the amplitude-modulated signal comprsies a squarewave voltammetry process where a square wave is pulsed with a voltage bias having a step size between 3 mV to 8 mV, a pulse size between 15 mV to 45 mV, with a frequency between 10 Hz to 50 Hz is swept over a voltage range of between 0 V to 2 V.

* * * * *

UNITED STATES PATENT AND TRADEMARK OFFICE
CERTIFICATE OF CORRECTION

PATENT NO. : 12,416,592 B2  
APPLICATION NO. : 18/997293  
DATED : September 16, 2025  
INVENTOR(S) : Wesley Lawrence et al.

It is certified that error appears in the above-identified patent and that said Letters Patent is hereby corrected as shown below:

On the Title Page  
In item (57), Abstract     Lines 14-15,     change "signals to monitor" to --signals, to monitor--

In the Specification

| | | |
|---|---|---|
| Column 9, | Lines 15-16, | change "bis(trifluoromethyl) sulfonyl) imide;" to --bis(trifluoromethyl)sulfonyl)imide;-- |
| Column 9, | Lines 17-18, | change "bis(trifluoromethyl) sulfonyl) amide;" to --bis(trifluoromethyl)sulfonyl)amide;-- |
| Column 9, | Line 21, | change "bis(trifluoromethyl) sulfonyl)imide;" to --bis(trifluoromethyl)sulfonyl)imide;-- |
| Column 9, | Line 23, | change "bis(trifluoromethyl) sulfonyl)amide;" to --bis(trifluoromethyl)sulfonyl)amide;-- |
| Column 9, | Lines 26-27, | change "bis(trifluoromethyl) sulfonyl)imide;" to --bis(trifluoromethyl)sulfonyl)imide;-- |
| Column 9, | Lines 28-29, | change "bis(trifluoromethyl) sulfonyl)amide;" to --bis(trifluoromethyl)sulfonyl)amide;-- |
| Column 9, | Line 31, | change "bis(trifluoromethyl) sulfonyl);" to --bis(trifluoromethyl)sulfonyl);-- |
| Column 9, | Line 33, | change "bis(trifluoromethyl) sulfonyl)amide;" to --bis(trifluoromethyl)sulfonyl)amide;-- |
| Column 9, | Line 36, | change "bis(trifluoromethyl) sulfonyl)imide;" to --bis(trifluoromethyl)sulfonyl)imide;-- |
| Column 9, | Lines 38-39, | change "bis(trifluoromethyl) sulfonyl)amide;" to --bis(trifluoromethyl)sulfonyl)amide;-- |
| Column 9, | Lines 41-42, | change "bis(trifluoromethyl) sulfonyl)imide;" to --bis(trifluoromethyl)sulfonyl)imide;-- |
| Column 9, | Line 44, | change "bis(trifluoromethyl) sulfonyl)amide;" to --bis(trifluoromethyl)sulfonyl)amide;-- |
| Column 9, | Line 47, | change "1-propylpyrroldinium 1-methyl-1- |

Signed and Sealed this  
Twenty-first Day of October, 2025

John A. Squires  
*Director of the United States Patent and Trademark Office*

CERTIFICATE OF CORRECTION (continued)
U.S. Pat. No. 12,416,592 B2

|  |  |  | propylpyrroldinium bis" to --1-propylpyrroldinium bis-- |
|---|---|---|---|
|  | Column 9, | Line 48, | change "(trifluoromethyl) sulfonyl)imide; bis" to --(trifluoromethyl)sulfonyl)imide; 1-methyl-1-propylpyrroldinium bis-- |
|  | Column 10, | Line 2, | change "100 Hz to 1 MHZ," to --100 Hz to 1 MHz,-- |
| In the Claims |  |  |  |
| Claim 1, | Column 13, | Lines 22-23, | change "the frequency amplitude-modulated" to --the frequency- and amplitude-modulated-- |
| Claim 20, | Column 15, | Line 8, | change "signal comprsies a squarewave" to --signal comprises a squarewave-- |
| Claim 20, | Column 15, | Line 10, | change "pulse size between" to --pulse size of between-- |